US011420056B2

(12) United States Patent
Capogrosso et al.

(10) Patent No.: US 11,420,056 B2
(45) Date of Patent: Aug. 23, 2022

(54) SYSTEM FOR PLANNING AND/OR PROVIDING NEUROMODULATION, ESPECIALLY NEUROSTIMULATION

(71) Applicants: ECOLE POLYTECHNIQUE FEDERALE DE LAUSANNE (EPFL), Lausanne (CH); ONWARD MEDICAL N.V., Eindhoven (NL)

(72) Inventors: Marco Capogrosso, Lausanne (CH); Karen Minassian, Vienna (AT); Fabien Wagner, Lausanne (CH); Gregoire Courtine, Lausanne (CH); Miroslav Caban, Eindhoven (NL); Robin Brouns, Eindhoven (NL); Jurriaan Bakker, Eindhoven (NL); Andre Kleibeuker, Eindhoven (NL); Bert Bakker, Eindhoven (NL); Vincent Delattre, Eindhoven (NL)

(73) Assignees: ECOLE POLYTECHNIQUE FEDERALE DE LAUSANNE (EPFL), Lausanne (CH); ONWARD MEDICAL N.V., Eindhoven (NL)

( * ) Notice: Subject to any disclaimer, the term of this patent is extended or adjusted under 35 U.S.C. 154(b) by 16 days.

(21) Appl. No.: 16/769,525

(22) PCT Filed: Nov. 29, 2018

(86) PCT No.: PCT/EP2018/082948
§ 371 (c)(1),
(2) Date: Jun. 3, 2020

(87) PCT Pub. No.: WO2019/110402
PCT Pub. Date: Jun. 13, 2019

(65) Prior Publication Data
US 2020/0391030 A1    Dec. 17, 2020

(30) Foreign Application Priority Data

Dec. 5, 2017    (EP) ................................ 17205363

(51) Int. Cl.
*A61N 1/36*    (2006.01)
*A61N 1/05*    (2006.01)

(52) U.S. Cl.
CPC ....... *A61N 1/36062* (2017.08); *A61N 1/0551* (2013.01); *A61N 1/36135* (2013.01)

(58) Field of Classification Search
None
See application file for complete search history.

(56) References Cited

U.S. PATENT DOCUMENTS

2007/0150023 A1    6/2007    Ignagni et al.
2008/0027346 A1    1/2008    Litt et al.
(Continued)

FOREIGN PATENT DOCUMENTS

EP    2810689 A1    12/2014
EP    2810690 A1    12/2014

OTHER PUBLICATIONS

Bizzi, E. et al., "Modular Organization of Motor Behavior," Trends in Neurosciences, vol. 18, No. 10, Oct. 1995, 8 pages.
(Continued)

*Primary Examiner* — Michael W Kahelin
*Assistant Examiner* — Elizabeth K So
(74) *Attorney, Agent, or Firm* — McCoy Russell LLP

(57) ABSTRACT

The present invention relates to methods and systems for planning and/or providing neuromodulation. An example system comprises
a neurostimulator comprising a least one electrode,
functional mapping module configured and arranged such that based on stimulation related basic data and stimulation related response data and transfer data a digital characteristic (Continued)

functional map is generated and/or provided, which describes the interrelation between the stimulation related basic data and the stimulation related response data and the transfer data, and analysis module configured and arranged such that the digital characteristic functional map may be analyzed in connection with neurostimulation provided by the neurostimulator such that the provided neurostimulation and its response may be analyzed on the basis of the functional map and that on the basis of this analysis a placement analysis of a placement of the electrode is provided.

13 Claims, 9 Drawing Sheets

(56) References Cited

U.S. PATENT DOCUMENTS

| | | |
|---|---|---|
| 2013/0116751 A1 | 5/2013 | Moffitt et al. |
| 2015/0066111 A1 | 3/2015 | Blum et al. |
| 2016/0001096 A1 | 1/2016 | Mishelevich |
| 2016/0030750 A1 | 2/2016 | Bokil et al. |
| 2016/0143588 A1 | 5/2016 | Hoitink et al. |

OTHER PUBLICATIONS

Rattay, F. et al., "Epidural electrical stimulation of posterior structures of the human lumbosacral cord: 2. quantitative analysis by computer modeling," Spinal Cord, vol. 38, No. 8, Aug. 2000, 17 pages.

Minassian, K. et al., "Stepping-like movements in humans with complete spinal cord injury induced by epidural stimulation of the lumbar cord: electromyographic study of compound muscle action potentials," Spinal Cord, vol. 42, No. 7, Jul. 2004, Published Online May 4, 2004, 16 pages.

Gerasimenko, Y. et al., "Spinal cord reflexes induced by epidural spinal cord stimulation in normal awake rats," Journal of Neuroscience Methods, vol. 157, No. 2, Oct. 30, 2006, Published Online Jun. 9, 2006, 11 pages.

Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.

Harkema, S. et al., "Effect of Epidural stimulation of the lumbosacral spinal cord on voluntary movement, standing, and assisted stepping after motor complete paraplegia: a case study," Lancet, vol. 377, No. 9781, Jun. 4, 2011, Available Online May 19, 2011, 17 pages.

Van Den Brand, R. et al., "Restoring Voluntary Control of Locomotion after Paralyzing Spinal Cord Injury," Science Magazine, vol. 336, No. 6085, Jun. 1, 2012, 5 pages.

Capogrosso, M. et al., "A Computational Model for Epidural Electrical Stimulation of Spinal Sensorimotor Circuits," Journal of Neuroscience, vol. 33, No. 49, Dec. 4, 2013, 15 pages.

Levine, A. et al., "Identification of cellular node for motor control pathways," Nature Neuroscience, vol. 17, No. 4, Apr. 2014, Available Online Mar. 9, 2014, 22 pages.

Angeli, C. et al., "Altering spinal cord excitability enables voluntary movements after chronic complete paralysis in humans," Brain: A Journal of Neurology, vol. 137, No. 5, May 1, 2014, Published Online Apr. 8, 2014, 16 pages.

Danner, S. et al., "Human spinal locomotor control is based on flexibly organized burst generators," Brain: A Journal of Neurology, vol. 138, No. 3, Mar. 1, 2015, Published Online Jan. 12, 2015, 12 pages.

Shamir, R. et al., "Machine learning approach to optimizing combined stimulation and medication therapies for Parkinson's disease," Brain Stimulation, vol. 8, No. 6, Nov. 2015, Published Online Jun. 15, 2015, 22 pages.

Gerasimenko, Y. et al., "Noninvasive Reactivation of Motor Descending Control after Paralysis," Journal of Neurotrauma, vol. 32, No. 24, Dec. 15, 2015, Published Online Aug. 20, 2015, 13 pages.

Wenger, N. et al., "Spatiotemporal neuromodulation therapies engaging muscle synergies improve motor control after spinal cord injury," Natural Medicine, vol. 22, No. 2, Feb. 2016, Available Online Jan. 18, 2016, 33 pages.

Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Available Online Feb. 4, 2016, 16 pages.

Capogrosso, M. et al., "A Brain-Spinal Interface Alleviating Gait Deficits after Spinal Cord Injury in Primates," Nature, vol. 539, No. 7628, Nov. 10, 2016, 39 pages.

ISA European Patent Office, International Search Report and Written Opinion Issued in Application No. PCT/EP2018/082948, dated Feb. 5, 2019, WIPO, 9 pages.

SYSTEM FOR PLANNING AND/OR PROVIDING NEUROMODULATION, ESPECIALLY NEUROSTIMULATION

CROSS-REFERENCE TO RELATED APPLICATIONS

The present application is a U.S. National Phase of International Patent Application Ser. No. PCT/EP2018/082948; entitled "SYSTEM FOR PLANNING AND/OR PROVIDING NEUROMODULATION, ESPECIALLY NEUROSTIMULATION," filed on Nov. 29, 2018. International Patent Application Serial No. PCT/EP2018/082948 claims priority to European Patent Application No. 17205363.9, filed on Dec. 5, 2017. The entire contents of each of the above-referenced applications are hereby incorporated by reference for all purposes.

TECHNICAL FIELD

The present invention relates to a system for planning and/or providing neuromodulation, especially neurostimulation.

BACKGROUND AND SUMMARY

Decades of research in physiology have demonstrated that the mammalian spinal cord embeds sensorimotor circuits that produce movement primitives (cf. Bizzi, E., et al., *Modular organization of motor behavior in the frog's spinal cord.* Trends in neurosciences 18, 442-446 (1995); Levine, A. J. et al. *Identification of a cellular node for motor control pathways.* Nature neuroscience 17, 586-593, (2014)). These circuits process sensory information arising from the moving limbs and descending inputs originating from various brain regions in order to produce adaptive motor behaviours.

A spinal cord injury (SCI) interrupts the communication between the spinal cord and supraspinal centres, depriving these sensorimotor circuits from the excitatory and modulatory drives necessary to produce movement.

A series of studies in animal models and humans showed that electrical neuromodulation of the lumbar spinal cord using epidural electrical stimulation (EES) is capable of (re-)activating these circuits. For example, EES has restored coordinated locomotion in animal models of SCI, and isolated leg movements in individuals with motor paralysis (cf. van den Brand R, et al., *Restoring Voluntary Control of Locomotion after Paralyzing Spinal Cord Injury.* Science 336, 1182-1185 (2012); Angeli C A, et al., *Altering spinal cord excitability enables voluntary movements after chronic complete paralysis in humans.* Brain: a journal of neurology 137, 1394-1409 (2014); Harkema S, et al., *Effect of epidural stimulation of the lumbosacral spinal cord on voluntary movement, standing, and assisted stepping after motor complete paraplegia: a case study.* The Lancet 377, 1938-1947; Danner S M, et al., *Human spinal locomotor control is based on flexibly organized burst generators.* Brain: a journal of neurology 138, 577-588 (2015); Courtine G, et al., *Transformation of nonfunctional spinal circuits into functional states after the loss of brain input.* Nature neuroscience 12, 1333-1342, (2009); Capogrosso M, et al., *A brain-spine interface alleviating gait deficits after spinal cord injury in primates.* Nature 539, 284-288, (2016)).

Computational models (cf. Capogrosso M, et al., *A computational model for epidural electrical stimulation of spinal sensorimotor circuits.* The Journal of neuroscience: the official journal of the Society for Neuroscience 33, 19326-19340 (2013); Moraud E M, et al., *Mechanisms Underlying the Neuromodulation of Spinal Circuits for Correcting Gait and Balance Deficits after Spinal Cord Injury.* Neuron 89, 814-828 (2016); Rattay F, et al., *Epidural electrical stimulation of posterior structures of the human lumbosacral cord: 2. quantitative analysis by computer modeling.* Spinal cord 38, 473-489 (2000)) and experimental studies (cf. Gerasimenko Y, et al., Program No. 447.445 (Soc. Neurosci. Abstr.); Minassian K, et al., *Human lumbar cord circuitries can be activated by extrinsic tonic input to generate locomotor-like activity.* Human Movement Science 26, 275-295 (2007)) have provided evidence suggesting that EES recruits large-diameter sensory afferents, especially proprioceptive circuits (cf. Moraud E M, et al., *Mechanisms Underlying the Neuromodulation of Spinal Circuits for Correcting Gait and Balance Deficits after Spinal Cord Injury.* Neuron 89, 814-828, (2016)).

Consequently, the stimulation leads to the activation of motoneurons through mono- and polysynaptic proprioceptive circuits, as well as increases the general excitability of the lumbar spinal cord. In addition, the natural modulation of proprioceptive circuits during movement execution gates the effects of EES towards functionally relevant spinal pathways. Concretely, due to phase-dependent modulation of proprioceptive circuits, the effects of stimulation are restricted to specific ensembles of leg motoneurons that are coherent with the phase of the movement (cf. Moraud E M, et al., *Mechanisms Underlying the Neuromodulation of Spinal Circuits for Correcting Gait and Balance Deficits after Spinal Cord Injury.* Neuron 89, 814-828 (2016)).

Moreover, since EES engages motoneurons through trans-synaptic mechanisms, residual inputs from supraspinal centres are also capable of gating the effects of EES towards specific circuits or increasing the excitability of the motoneuron pools (and thus their responsiveness to EES) in order to mediate voluntary modulation of leg movements (cf. van den Brand R, et al., *Restoring Voluntary Control of Locomotion after Paralyzing Spinal Cord Injury.* Science 336, 1182-1185 (2012); Angeli C A, et al., Altering spinal cord excitability enables voluntary movements after chronic complete paralysis in humans. Brain: a journal of neurology 137, 1394-1409 (2014); Harkema, S, et al. Effect of epidural stimulation of the lumbosacral spinal cord on voluntary movement, standing, and assisted stepping after motor complete paraplegia: a case study. The Lancet 377, 1938-1947).

This conceptual framework was exploited to design a neuromodulation strategy that targets specific ensembles of proprioceptive afferents associated with flexion and extension of both legs (cf. Bizzi E, et al., *Modular organization of motor behavior in the frog's spinal cord.* Trends in neurosciences 18, 442-446 (1995); Levine A J, et al. *Identification of a cellular node for motor control pathways.* Nature neuroscience 17, 586-593 (2014)).

This strategy, termed spatiotemporal neuromodulation, consists of delivering EES bursts through targeted electrode configurations with a temporal structure that reproduces the natural activation of leg motoneurons during locomotion. This spatiotemporal neuromodulation therapy reversed leg paralysis in both rodent and primate models of SCI (cf. Capogrosso M, et al., *A brain-spine interface alleviating gait deficits after spinal cord injury in primates.* Nature 539, 284-288, (2016); Wenger N, et al., Spatiotemporal neuromodulation therapies engaging muscle synergies improve motor control after spinal cord injury. Nat Med 22, 138-145 (2016)).

This conceptual framework is applicable to develop spatiotemporal neuromodulation therapies for enabling leg motor control in humans with SCI.

Generally speaking, known stimulation systems use either Central Nerve System (CNS) stimulation, especially Epidural Electrical Stimulation (EES), or Peripheral Nerve System (PNS) Stimulation, especially Functional Electrical Stimulation (FES).

Epidural Electrical Stimulation (EES) is known to restore motor control in animal and human models and has more particularly been shown to restore locomotion after spinal cord injury by artificially activating the neural networks responsible for locomotion below the spinal cord lesion (cf. Capogrosso M, et al., *A Computational Model for Epidural Electrical Stimulation of Spinal Sensorimotor Circuits,* Journal of Neuroscience 4 Dec. 2013, 33 (49) 19326-19340; Courtine G, et al., *Transformation of nonfunctional spinal circuits into functional states after the loss of brain input,* Nat Neurosci. 2009 October; 12(10): 1333-1342; Moraud E M, et al, *Mechanisms Underlying the Neuromodulation of Spinal Circuits for Correcting Gait and Balance Deficits after Spinal Cord Injury,* Neuron Volume 89, Issue 4, p 814-828, 17 Feb. 2016). EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies. The produced movement is functional; however, due to relatively poor selectivity (network activation instead of selective targeting of key muscles) the controllability is low and the imprecisions hinder fluidity and full functionality in the potential space of the movement.

Peripheral Nerve System (PNS) Stimulation systems used to date in the clinic are known as Functional Electrical Stimulation (FES) that provides electrical stimulation to target muscles with surface electrodes, either directly through stimulation of their motorfibers (neuro-muscular stimulation), or through a limited set reflexes (practically limited to the withdrawal reflex) or by transcutaneously stimulating the peripheral nerves. The resulting muscle fatigue has rendered FES unsuitable for use in daily life. Furthermore, successes have remained limited through cumbersome setups when using surface muscle stimulation, unmet needs in terms of selectivity (when using transcutaneous nerve stimulation) and a lack of stability (impossible to reproduce exact electrode placement on a daily basis when stimulating muscles, moving electrodes due to clothes, sweating).

US 2016/030750 A1 discloses a computer implemented system and method facilitates the generation, sharing and refinement of volumes to stimulate anatomical tissue, such as spinal cord stimulation. The computer system analyses the volumes as well. More specifically, a computer implemented system and method facilitates a cycle of generation, sharing, and refinement of volumes related to stimulation of anatomical tissue, such as brain or spinal cord stimulation. Such volumes can include target stimulation volumes, side effect volumes, and volumes of estimated activation. A computer system and method also facilitates analysis of groups of volumes, including analysis of differences and/or commonalities between different groups of volumes.

US 2016/001096 A1 describes methods and systems that use multiple tharepeutic modalities to cause deep or superficial deep-brain stimulation. Methods for treatment of clinical conditions and physiological impacts are described, as well as methods for Guided Feedback control of non-invasive deep brain or superficial neuromodulator, as well as the non-invasive neuromodulation of the spinal cord by ultrasound energy.

EP 2 810 689 A1 and EP 2 810 690 A1 describe a system for planning and providing a therapy for Deep Brain neural applications, especially neurostimulation and/or neurorecording with at least one lead with a plurality of electrodes. The invention concerns a method for focusing the stimulation field provided by an active contact of a lead.

US 2015/066111 A1 discloses a tool for assisting in the planning or performing of electrical neuromodulation of a patient's spinal cord by calculating a volume of activation, registering electrodes and their position.

Current systems for neuromodulation in the field of the treatment of spinal cord injuries (SCI), for example after trauma or stroke or illness, have to match each input signal to a specific reaction of the patient. This can be quite time-consuming and also exhaustive for the patient to be treated and also for the physician and medical support staff. Also, the correct placement of electrodes is an important point.

This object is solved according to the present invention by a system for planning and/or providing neuromodulation, especially neurostimulation, with the features of claim 1. Accordingly, a system for planning and/or providing neuromodulation, especially neurostimulation is provided, comprising a neurostimulator comprising a least one electrode, functional mapping module configured and arranged such that based on stimulation related basic data and stimulation related response data and transfer data a digital characteristic functional map is generated and/or provided, which describes the interrelation between the stimulation related basic data and the stimulation related response data and the transfer data, and analysis module configured and arranged such that the digital characteristic functional map can be analyzed in connection with neurostimulation provided by the neurostimulator such that the provided neurostimulation and and its response can be analyzed on the basis of the functional map and that on the basis of this analysis an placement analysis of the placement of the electrode is provided.

The invention is based on the basic idea that on the basis of a functional mapping, which describes stimulation input, the link with the respective output and on the basis of data in connection with the electrode placement of a neurostimulator this placement of the electrode (S) is analyzed by the system and this analyze is provided to the user of the system. By this, the placement of the electrode of a neurostimulator may be assessed and guidance for the user when placing the electrode can be provided.

The invention may be further based on the basic idea that the multi-dimensional relationship between the stimulation signal and the patient response shall be described by a digital characteristic map, which forms a kind of functional mapping. This functional mapping describes inter alia the relationship in a specific situation at a specific point of time of stimulation input provided and the respective resulting output, which is for example a patient response e.g. in form of movement. In other words, the connection and transformation of a specific input signal, i.e. a stimulation input, and the respective output signal, i.e. the reaction and/or movement of the subject/patient is compiled and the respective data are collected. Then, these data describe as a kind of multidimensional map the respective reaction of the patient of specific input at a specific point of time. Such specific input at a specific point of time can be for example the abovementioned spatiotemporal stimulation. By creating and establishing the multidimensional map spatiotemporal stimulation input and the respective output, i.e. the respective patient reaction, a spatiotemporal stimulation can be configured for specific scenarios related to specific movements of or tasks to be performed by the patient like sitting, standing up (sit to stand), standing, walking, climbing stairs, stop walking, stand to sit. So, by using the multidimensional map in connection with spatiotemporal stimulation protocols can be created and provided, which are directly translatable to the design of spatiotemporal neuromodulation therapies to reverse inter alia leg paralysis. The digital characteristic map may be a curve, a plurality of curves or a landscape, e.g. a three-dimensional or even multi-dimensional landscape of a plurality of curves, which describe the dependencies between one specific input and one specific output at a certain point of time a pre-defined position. So, it is also possible that the landscape is changing its shape in dependency over the time.

In connection with the system specific kind of data are used.

In particular, there are stimulation related basic data. The stimulation related basic data are data that describe the stimulation in greater detail, in particular which kind of stimulation, which elements used for the stimulation and also the characteristics of a patient receiving the stimulation is present and/or used. Thus, the stimulation related basic data may define parameters of a neurostimulation system for treating a patient.

Moreover, there are stimulation related response data. The stimulation related response data describe, what kind of response is received in connection with the stimulation. In particular, these kind of data describe results of any kind triggered and received as response by the provided stimulation. Such stimulation related response data may include (but are not limited to) data describing activation of the spinal cord as response to the stimulation or specific movements and/or reactions of the patient induces by the neurostimulation. The stimulation related response data may inter alia comprise date of the activation of the spinal cord as response to the stimulation.

Also, there are transfer data. The transfer data are building a bridge between the stimulation related basic data and the stimulation related response data. There may be link data and/or translation data or a artificial response data, which may fill gaps, where no direct link between an input and an output is given. In particular artificial response data might be for example but not limited to extrapolation data or calculated data. The transfer data may comprise artificial response data and/or link data and/or translation data, which link and/or translate at least partially the stimulation related basic data and the stimulation related response data with each other.

The invention can also be used in the context of neuromodulation, especially neurostimulation, where the electrical stimulation parameters defining the stimulation for the subject to be treated can vary cyclically over time in a pre-programmed manner, i.e. one cycle with pre-defined timings for the various stimulation patterns is repeated over and over again.

Such neuromodulation approaches may cover (but are not limited to) invasive or non-invasive or mixed approaches. They may be based on neurostimulation only. Also, pharmacological approaches or the like shall be covered and understood by the term neuromodulation. Neurostimulation may be applied epidurally and/or subdurally and/or transcutaneously or in another suitable manner.

The use of pre-programmed temporal stimulation pattern data together with the use of pre-programmed spatial stimulation pattern data allow a stimulation at the correct place at the correct time to facilitate, enable or trigger the intended action of the subject. Such an action can be movement of extremities like feet and/or legs and/or arms, contraction and/or relaxation and/or any movement of muscles in connection with movement of the subject or cardiovascular functions of the subject, e.g. blood pressure control and/or blood circulation support and/or blood circulation control. Such an approach can be characterized as open-loop phasic stimulation. Basically, it forms a way to stimulate phasically the nervous system, especially the spinal cord of a subject or patient without the need for complex and/or complicated feedback systems. It can easily be implemented to promote locomotion, cyclical activity with physical training devices and reduce orthostatic hypotension, after nervous system impairments such as spinal cord injury. So it is possible to improve a neuromodulation system, e.g. in the field of improving recovery after neurological disorders like spinal cord injury (SCI), for example after trauma or stroke or illness, especially in that neuromodulation and/or neurostimulation can be provided in almost any environment and in daily life, adapted to the patient's needs and providing the needed assistance in training and daily life for the patient, also adjusted to the progress of the rehabilitation of the patient.

The mapping module may be configured and arranged such that the digital characteristic map is generated automatically. By generating the digital characteristic map automatically a very efficient and time-consuming procedure as now in the state of the art may be overcome. The dependencies between input and output can be generated faster and more efficient. The automatic generation process may contain steps like interpolation or the use of plausible assumptions based on known biophysical or physiological relations. There may be an algorithm that uses iterations to find the most suitable way to describe at least parts of the digital characteristic map.

Furthermore, the stimulation related basic data may comprise at least one selected from
  electrode data, and/or
  stimulation characteristic data, and/or
  patient data, and/or
  stimulation data, and/or
  treatment application data.

These kind of data and/or parameters describe in a very clear and well-defined way the circumstances and variables of the stimulation to be provided or the provided stimulation. With this kind of data the input situation in dependency of the time can be described. Generally, further parameters may also be used independently, alternatively or additionally.

Additionally, the stimulation related response data may comprise data comprise at least one selected from
  sequence of events data, and/or
  motion data, and/or
  EMG data, and/or
  afferent signal data, and/or
  efferent signal data, and/or
  impedance data, and/or
  EEG data, and/or
  BCI data.

This kind of data and/or parameters describe in a very clear and well-defined way the circumstances and variables of the result or output caused by the stimulation to be provided or the provided stimulation. With this kind of data the output situation in dependency of the time can be described. Generally, further parameters may also be used independently, alternatively or additionally.

Also, the transfer module may be configured and arranged such that at least one kind of data selected from
body posture data, and/or
static and/or dynamic data, and/or
task and/or activity data, and/or
time and/or delay data, and/or
rehabilitation data, and/or
drug treatment data, and/or
data related to the voluntariness of movement,
is or are used to generate the transfer data.

The transfer data may be used to prepare the relationship between the stimulation related basic data and the stimulation related response data. The transfer data may also be used to fill gaps, where there is no pair between stimulation related basic data and stimulation related response data.

In particular, where there is no matching stimulated related response data to specific stimulation related basic data, by means of the transfer data, stimulation related response data may be calculated and vise versa. On the basis of the stimulation related basic data, the stimulation related response data and the transfer data, a fully fletched picture of the interrelationship between stimulation related basic data and stimulation related response data may be created. This kind of picture or mapping consists of real data and also for example calculated and/or virtual data.

The virtual mapping module allows to directly generate the digital characteristic map virtually online, which is enhancing the process of mapping the stimulation related basic data and the stimulation related response data.

The system may further comprise a stimulation related basic data storage module for storing the stimulation related basic data defining parameters of the neurostimulator for treating a patient, the stimulation related basic data storage module comprising at least one set of stimulation related basic data and/or working parameters of the neurostimulator. The stimulation related basic data may be data that describe the stimulation in greater detail, in particular which kind of stimulation, which elements of the neurostimulator are used for the stimulation and also the characteristics of the patient receiving the stimulation may be present and/or used. In particular, also the number of electrodes, the shape of the electrode or the schematical layout of or data defining an electrode array or the like may be provided. Also, there may be stimulation patterns and the activated and non-activated electrodes stored as stimulation related basic data. Thus, stimulation related basic data may define parameters of the neurostimulator for treating a patient.

Additionally, the system may further comprise a stimulation related response data storage module for storing the stimulation related response data, the stimulation related response data storage module comprising at least one set of stimulation related response data including activation to at least a part of the neural system, especially of the spinal cord, as response to stimulation provided to the neural system, especially to the spinal cord. The stimulation related response data may describe, what kind of response is received in connection with the stimulation. In particular, these kind of data describe results of any kind triggered and received as response by the provided stimulation. Such stimulation related response data may include (but are not limited to) data describing activation of the spinal cord as response to the stimulation or specific movements and/or reactions of the patient induced by neurostimulation. The stimulation related response data may inter alia comprise data of the activation of the spinal cord as response to the stimulation.

Also, the system may further comprise a transfer module configured and arranged such that the stimulation related basic data received by the data input module are linked and/or translated into and/or with the response data or artificial response data created by the transfer module, wherein the data generated by the transfer module are transfer data, the transfer data comprising link data and/or translation data and/or artificial response data and/or reference data, and a transfer response data storage module for storing the transfer data. The transfer data may be building a bridge between the stimulation related basic data and the stimulation related response data. There may be linked data and/or translation data or artificial response data, which may fill gaps, where no direct link between an input and an output is given. In particular, artificial response data might be for example but not limited to extrapolation data or calculated data. The transfer data may comprise artificial response data and/or linked data and/or translation data, which link or translate at least partially the stimulation related basic data and the stimulation related response data with each other.

Furthermore, the system may further comprise a visualization module. Such a visualization module may at least comprise a display or any other output module, for example loudspeakers, beamer, projectors of any kind or the like. With the visualization module information may be output to a user and visualized.

The visualization module may be configured and arranged such that at least partially stimulation related basic data and at least partially stimulation related response data may be displayed.

The visualization module may be configured and arranged such that the stimulation related response data may be visualized at least schematically with representations of muscles or muscles groups receiving neurostimulation. For example, schematically representations of the muscle groups in connection with the outlines of the human body may be displayed and activated/stimulated muscle groups may be displayed with another color then unstimulated muscle groups.

The system may comprise stimulation related response data input elements and the system may be configured and arranged such that an inverse control is provided by inputting stimulation related response data via the stimulation related response data input elements and that the system further comprises selection elements, which are configured and arranged such that based on the digital characteristic functional map suitable stimulation related basic data may be selected. The input elements may be for example a touchscreen, input elements of a computer like a keyboard or a mouse or a touchpad or the like. By inverse control the user may be for example select the muscle groups to be stimulated and then the respective stimulation settings may be automatically provided by the system.

Furthermore, the system may comprise a neuromodulation settings generation module, which is configured and arranged to translate the digital characteristic functional map into neuromodulation parameter settings for a neuromodulation treatment of a subject. Here, a result based planning may be done, i.e. by selecting the respective results and the stimulation result achieved, the necessary parameter settings may be selected automatically by the system. In other words, by defining the desired output, the necessary input data will be found by the system.

The neuromodulation settings generation module may comprise a transfer interface, which is configured and arranged for transferring neuromodulation parameter settings from the system to a neuromodulation device. Such a neuromodulation device may be for example an implanted neurostimulator. There may be for example a transcutaneous transfer interface, for example a wireless transfer system by using RF-technology, inductance, ultrasound or the like.

The analysis module may be configured and arranged such that on the basis of the functional map and the placement analysis a placement proposal is generated. For example, such a placement proposal may include information about the current placement of the electrode or electrodes and a proposal, how to change the placement. For example, directions for change of placements may be provided, like to the left, to the right or by just displaying arrows.

In particular, it is possible that the placement proposal may be displayed by the visualization module. Here, the placement may be displayed in connection with the spinal cord and the spine, for example by superimposing as schematically representation of the electrodes or the electrode array over the spinal cord and the bone structure of the spine. Then by displaying arrows and a schematically traffic light the placement proposal may be displayed and for example in real-time the correction of the placement may be guided by the system.

BRIEF DESCRIPTION OF THE FIGURES

Further details and advantages of the present invention shall now be disclosed in connection with the drawings.

It is shown in

FIG. 3a-k several details of the anatomical structures to be stimulated and anatomical structures of interest;

DETAILED DESCRIPTION

System Description

Figure 1:
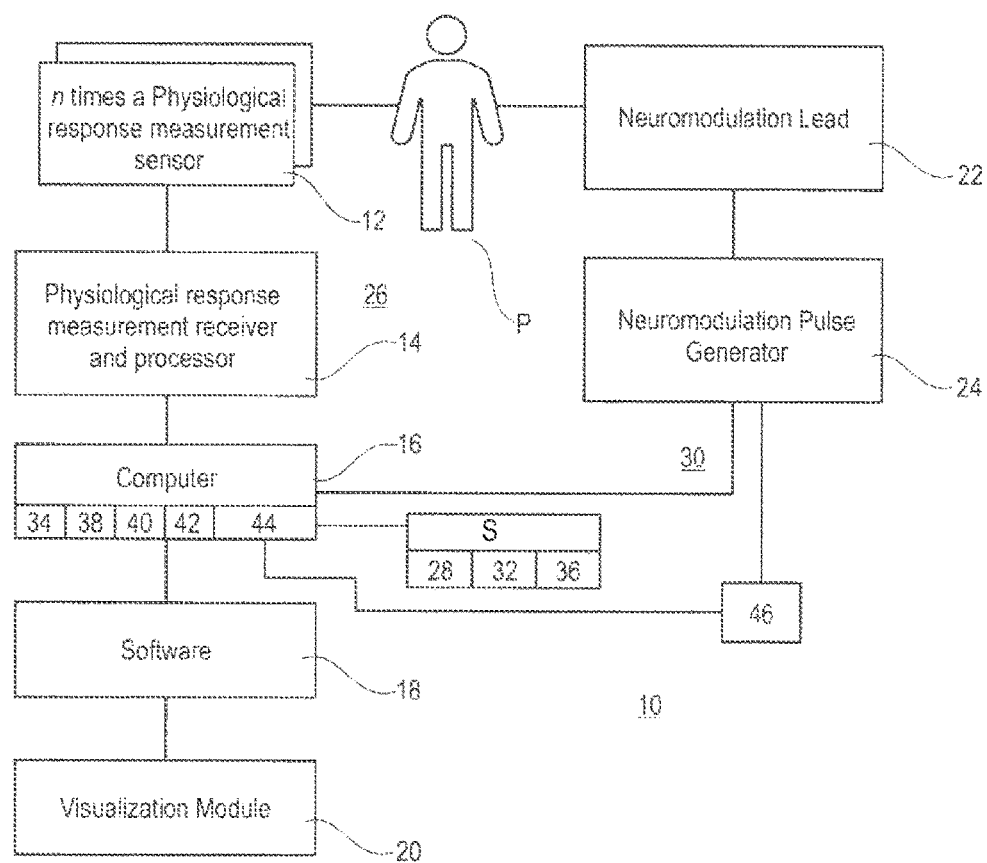
FIG. 1 a schematical overview of a possible embodiment for a system for planning and/or providing neuromodulation.

FIG. 1 shows as schematical overview of a possible embodiment for a system for planning and/or providing neuromodulation, here neurostimulation according to the present invention.

The patient P is connected to the system 10.

The system 10 comprises at least:
a physiological response measurement sensor 12
a physiological response measurement receiver and processor 14
a computer 16
a software 18
a visualization module 20
a neuromodulation lead 22 and neuromodulation pulse generator 24, which form together a neurostimulator in this embodiment.

The physiological response measurement sensor 12 and the physiological response measurement receiver processor 14 function as a first data input module 26 for stimulation related basic data.

The computer 16 and the software 18 are connected to a storage being part of the computer 16.

The storage S comprises a stimulation related basic data storage module 28 for storing the stimulation related basic data obtained by the first data input module 26 for stimulation related basic data.

The stimulation related basic data may comprise at least one (or more or all) selected from
electrode data, and/or
stimulation characteristic data, and/or
patient data, and/or
stimulation data, and/or
treatment application data.

In the shown embodiment, the neuromodulation lead 22, the neuromodulation pulse generator 24, the physiological response measurement sensor 12 and the physiological response measurement receiver and processor 14 form also a second data input module 30 for stimulated related response data.

The stimulation related response data are stored in a further stimulation related response data storage module 32, which is also part of the storage S.

The stimulation related response data comprise data comprise at least one (or more or all) selected from
sequence of events data, and/or
motion data, and/or
EMG (electromyography) data, and/or
afferent signal data, and/or
efferent signal data, and/or
impedance data, and/or
EEG (electroencephalograhy) data, and/or
BCI (brain control interface) data.

Moreover, the computer 16 comprises a transfer module 34.

The transfer module 34 is configured and arranged such that the stimulation related basic data received by the data input module are linked and/or translated into and/or with the response data and/or artificial response data created by the transfer module 34, wherein the data generated by the transfer module 34 are transfer data, the transfer data comprising link data and/or translation data and/or artificial response data.

The transfer module 34 may configured and arranged such that at least one kind of data selected from
body posture data, and/or
static and/or dynamic data, and/or
task and/or activity data, and/or
time and/or delay data, and/or
rehabilitation data, and/or
drug treatment data, and/or
data related to the voluntariness of movement,
is or are used to generate the transfer data.

Moreover, there is a transfer response data storage module for storing the transfer data, which is also part of the storage S.

Furthermore, the computer 16 comprises for creating a digital characteristic map 36 a mapping module 38.

The mapping module 38 is configured and arranged such that based on the stimulation related basic data and the stimulation related response data and the transfer data digital characteristic map 36 is generated, which describes the interrelation between the stimulation related basic data and the stimulation related response data and the transfer data.

The mapping module 38 may be configured and arranged such that the digital characteristic map 36 is generated automatically.

The system 10 may further comprise a virtual mapping module 40, which is configured and arranged to generate the digital characteristic map virtually online.

Moreover, the system 10 comprises a correlation and/or simulation module 42, which is configured and arranged to correlate on the basis of digital characteristic map by way of simulation the stimulation related basic data and the stimulation related response data and the transfer data.

The correlation and/or simulation module 42 is configured and arranged such that from a preselected stimulation related basic data the correlating stimulation related response data are identified. Also, from a preselected stimulation related response data the correlating stimulation related basic data may be identified.

The correlation and/or simulation module 42 also has the functionality of an analysis module or is embodied as analysis module 42. The analysis module can be also embodied as a separate module or element.

The system 10 further comprises a neuromodulation settings generation module 44, which is configured and arranged to translate the digital characteristic map into neuromodulation parameter settings for a neuromodulation treatment of a subject.

Furthermore, the neuromodulation settings generation module 44 comprises a transfer interface 46, which is configured and arranged for transferring neuromodulation parameter settings from the system to a neuromodulation device, here the Neuromodulation Pulse Generator 24.

The analysis module 42 is configured and arranged such that the digital characteristic functional map can be analyzed in connection with neurostimulation provided by the neurostimulator such that the provided neurostimulation and and its response can be analyzed on the basis of the functional map and that on the basis of this analysis an placement analysis of the placement of the electrode is provided.

The visualization module 20 is configured and arranged such that at least partially stimulation related basic data and at least partially stimulation related response data are displayed.

The visualization module 20 is configured and arranged such that stimulation related response data are visualized at least schematically with representations of muscles or muscles group receiving neurostimulation.

The system comprises stimulation related response data input module and that the system is configured and arranged such that an inverse control is provided by inputting stimulation related response data via the stimulation related response data input module and that system further comprises selection module, which are configured and arranged such that based on the digital characteristic map suitable stimulation related basic data are selected.

Also, the system comprises a neuromodulation settings generation module, which is configured and arranged to translate the digital characteristic map into neuromodulation parameter settings for a neuromodulation treatment of a subject.

The above system and process may be also set up as a self-learning or machine-learning process. Especially all kind of maps may be generated in a self-learning or machine-learning process.

Figure 2:
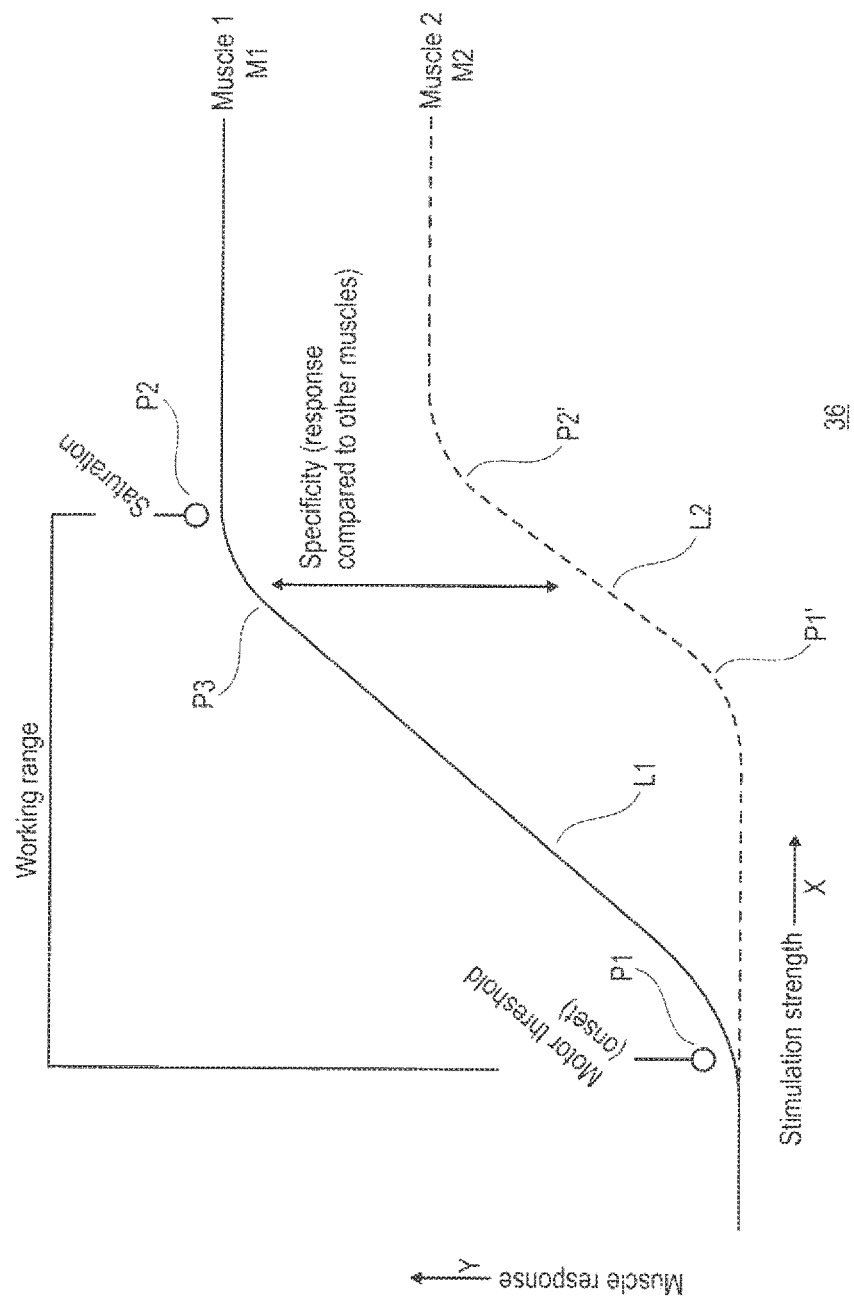
FIG. 2 a (two-dimensional/2D) part of the obtained digital characteristic map.

FIG. 2 shows in 2D a part of the obtained digital characteristic map 36, describing the interrelation between the stimulation related basic data and the stimulation related response data and the transfer data.

On the x-axis the stimulation strength is shown.

On the y-axis the muscle response is shown.

In the digital characteristic map 36, two lines L1 and L2 describing the connection between the stimulation strength (i.e. stimulation related basic data) with the muscle response (stimulation related response data), wherein the connection can be seen as kind of a transfer function (i.e. stimulation related transfer data).

The first line L1 is describing the stimulation response of a first muscle M1 and the dashed line L2 is describing the stimulation response for a second muscle M2.

As can be seen, at a point of stimulation P1 muscle M1 starts to react.

This point P1 is called motor threshold point or onset point.

At this point P1, muscle M2 shows no reaction.

Increasing the stimulation strength will result at some point in a saturation, this point being denoted as point P2, also called saturation point P2.

This point P2, being the saturation point is defining the point at which no further stimulation will receive in stronger muscle activity of muscle M1.

Thus, this point is called saturation point, as increasing the stimulation will not result in better stimulation results and muscle activity.

As can be seen, at point P1' a second muscle starts to react on the applied stimulation, however, at a lower level and with less activity. So, a specificity point P3 may be defined.

The specificity point P3 defines a point, where muscle M1 shows relatively high response, whereas the response of muscle M2, which is also stimulated by the applied stimulation shows less activity, which is still at a level that can be accepted, as it is not really relevant.

Also shown is the saturation point P2' for muscle M2.

FIG. 2 shows a part of digital characteristic map for example for a specific subset of electrodes of an electrode array that is placed in the vicinity of the spinal cord, for example to perform epidural electrical stimulation (EES). By already knowing the connection the placement of the electrodes vis-a-vis the spinal cord and the afferent sensory neurons, the necessary muscles or muscle groups needed for a specific movement can be addressed.

When generating the digital characteristic map, the user is confronted with a plurality of degrees of freedom.

Moreover, fast scans are limited by the response time of the muscles (approx. 2 s/0.5 hz).

This will lead to long mapping times for generating the digital characteristic map.

Thus, here optimization might be wanted.

This can be done by optimizing the patients specific mapping procedure, i.e. finding the optimal stimulation settings for a given task.

Therefore, the following options can be used alternatively or in combination:

By applying specific search function instead of a current step-wise approach, the time consuming step-wise approach can be avoided. Possible approaches in connection with this search function approach are particle swarm, genetic, steepest gradient, optimization algorithms.

A model fitting approach may be used. Here, a patient specific or generic model or the like may be used that predicts muscle response for a specific stimulation and uses the actual mapping to fine-tune and/or register and/or adapt this model to the individual/specific patient.

There may be a data base of patients. Here iterative/machine learning methods may be used for mappings from previous patients to suggest (patient-specific) stimulation settings, probabilistic/statistics can be used, e.g. if one use those settings, then the probability of an effective stimulation may be a certain percentage X % and the crosstalk may be another certain percentage Y %.

For the above three methods, certain quality indicators/optimization object functions may be used such as sensitivity index, cross-talk, muscle onset, muscle saturation or the like.

The above three approaches may improve the generation of the digital characteristic map (the so called mapping procedure) by:

reducing the mapping times creating patient specific optimum results potential reduction of the number of EMG's required, making the procedure easier and faster theoretically one can abandon the use of EMG's at all by fine-tuning of the used motion sensors.

FIG. 3a-k show several details of the anatomical structures to be stimulated and anatomical structures of interest.

FIG. 3a-e relates to the example of Rhesus monkeys.

FIG. 3f-k relate to rodents, here Louis rats.

Figure 3C:
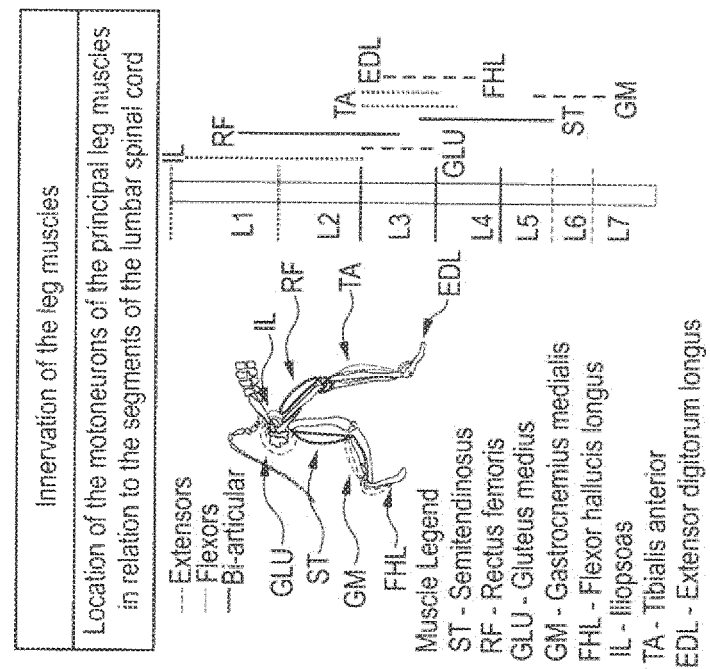
Figure 3B:
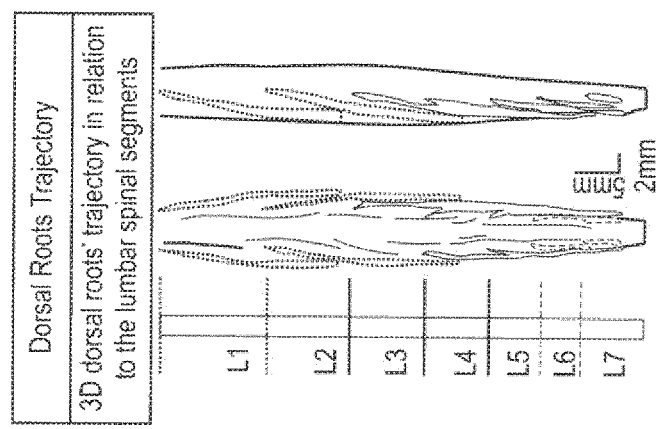
Figure 3A:
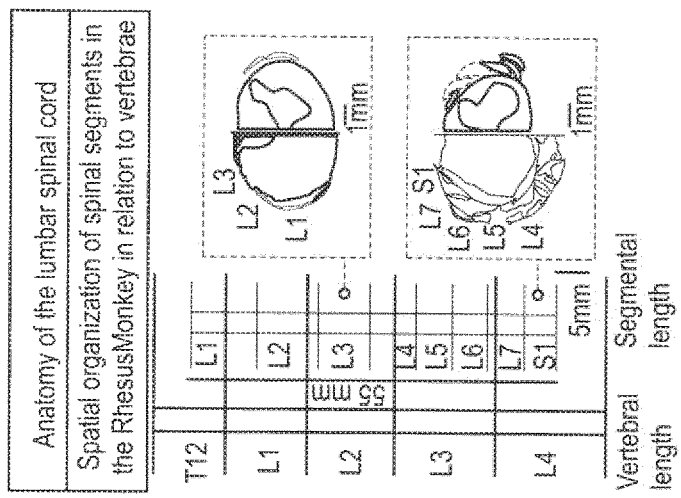

FIG. 3a shows the anatomy of the lumbar spinal cord of a Rhesus monkey to be stimulated.

Here this spatial organization of spinal segments of the Rhesus monkey in relation to the vertebrae is shown.

FIG. 3b shows the dorsal roots trajectory.

Here the 3D-dorsal roots' trajectory in relation to the lumbar spinal segment is shown.

FIG. 3c shows the innervation of leg muscles, in particular the location of the motor neurons of the principle leg muscles in relation to the segments of the lumbar spinal cord.

Shown are extensor muscles with the denotation EXT, flexor muscles with the reference sign FLEX and the articular muscles with the reference sign B.

The muscles are denoted as follows:

ST—SEMITENDINOSUS
RF—RECTUS FEMORIS
GLU—GLUTEUS MEDIUS
GM—GASTROCNEMIUS MEDIALES
FHL—FLEXOR HALLUCIS LONGUS
IL—ILIOPSOAS
TA—TIBIALIS ANTERIOR
EDL—EXTENSOR DIGITORUM LONGUS.

Figures 3D, 3E, 3F, 3G:
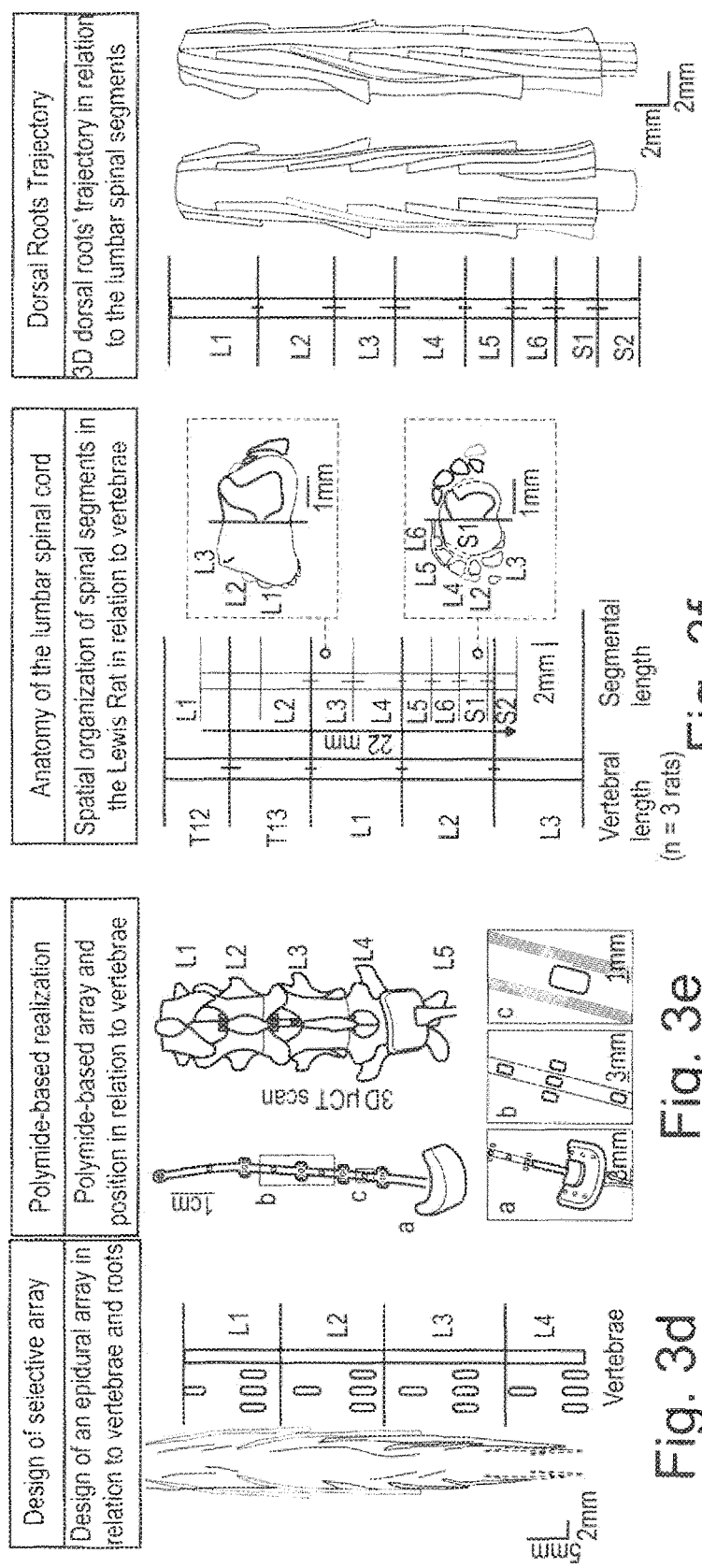

FIG. 3d shows the design of a selective array of electrodes of for example a neuromodulation lead 22.

Here, the design of an epidural array in relation to the vertebrae and roots of the spinal cord is shown.

FIG. 3e shows a polyamide-based realization.

Here, the polyamide-based array and position in relation to the vertebrae is shown.

FIG. 3f-k show respectively the corresponding drawings for rodents, here Lewis rats.

In particular, it is shown in

Figure 3K:
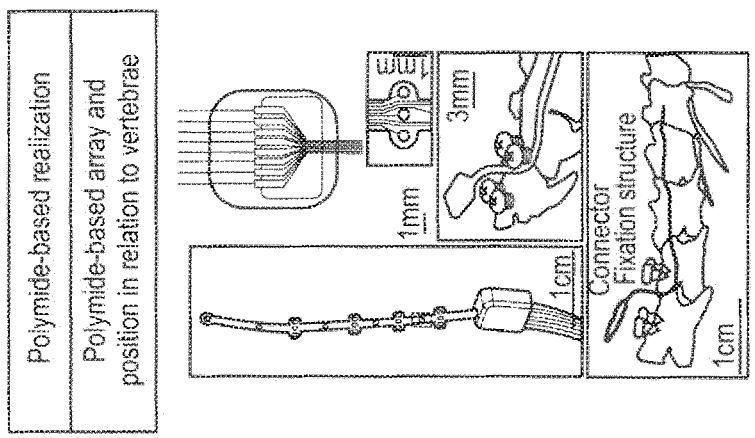
Figure 3I:
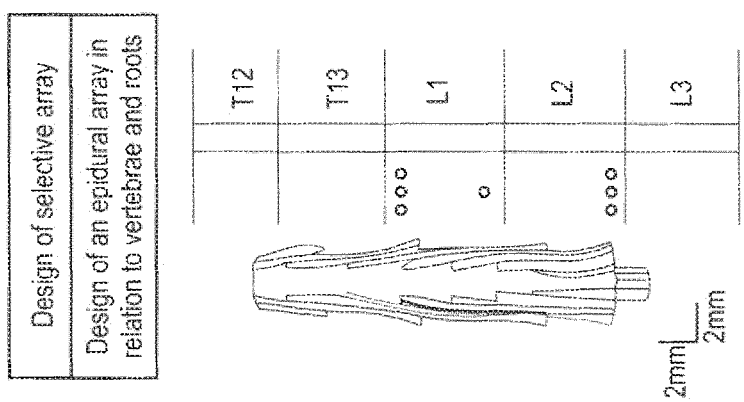
Figure 3H:
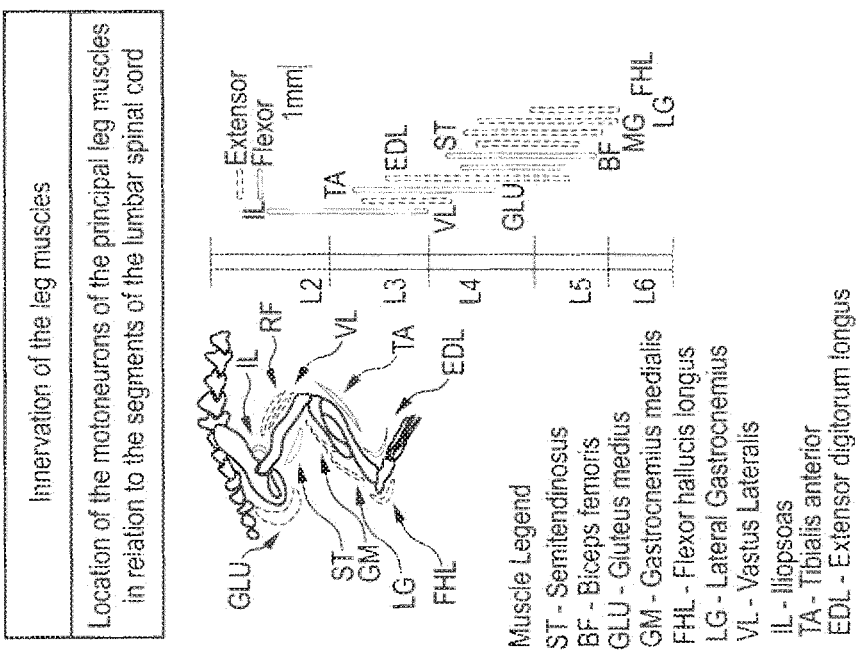

FIG. 3f the anatomy of the lumbar spinal cord of a rodent,
FIG. 3g the dorsal roots trajectory,
FIG. 3h the innervation of the leg muscles,
FIG. 3i the design of the selective array, and
FIG. 3k the polyamide-based realization.

Figure 4:
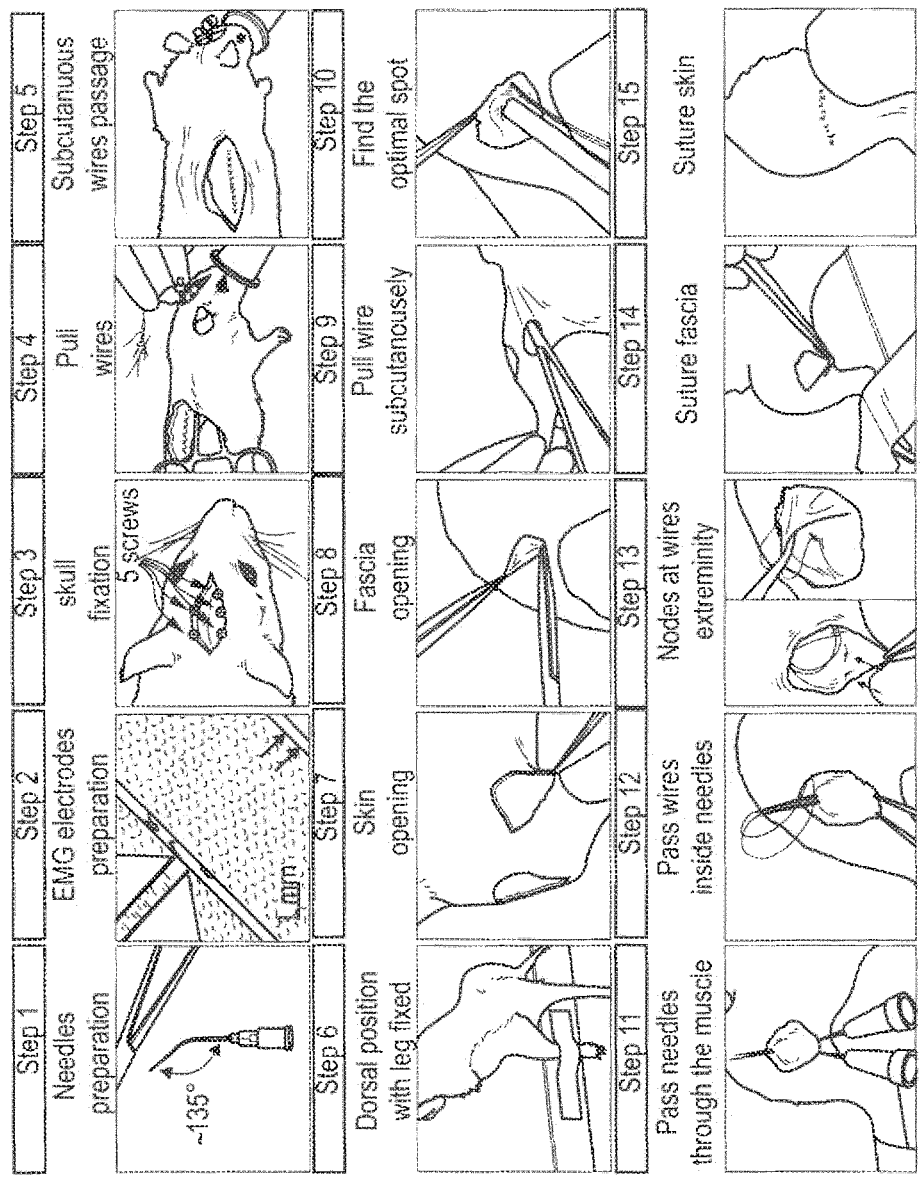
FIG. 4 the implantation procedure of a neuromodulation lead of a system according to FIG. 1, here in connection with the example of the implantation of a neuromodulation lead for a rodent (here a Lewis rat)

FIG. 4 shows the implantation procedure of the neuromodulation lead 22, here in connection with the example of the implantation of a neuromodulation lead for a rodent (here a Lewis rat).

The implantation of a neuromodulation lead for other mammals like monkeys or human beings is similar.

In step ST1 the needles are prepared.
In step ST2 the EMG electrodes are prepared.
In step ST3 a skull fixation is done.
In step ST4 the lead wires are pulled.
In step ST5 subcutaneous wire passage is prepared and provided.
In step ST6 a dorsal position with leg fixed is performed.
In step ST7 a skin opening is performed.
In step ST8 a fascia opening is performed.
In step ST9 the wires are subcutaneously pulled.
In step ST10 the optimal spot is found.
In step ST11 needles are passed through the muscles.
In step ST12 wires are passed inside the needles.
In step ST13 notes at wires extremity are provided.
In step ST14 the fascia is provided with a suture.
In step ST15 a suture to the skin is performed to close the implantation side.

Figure 5:
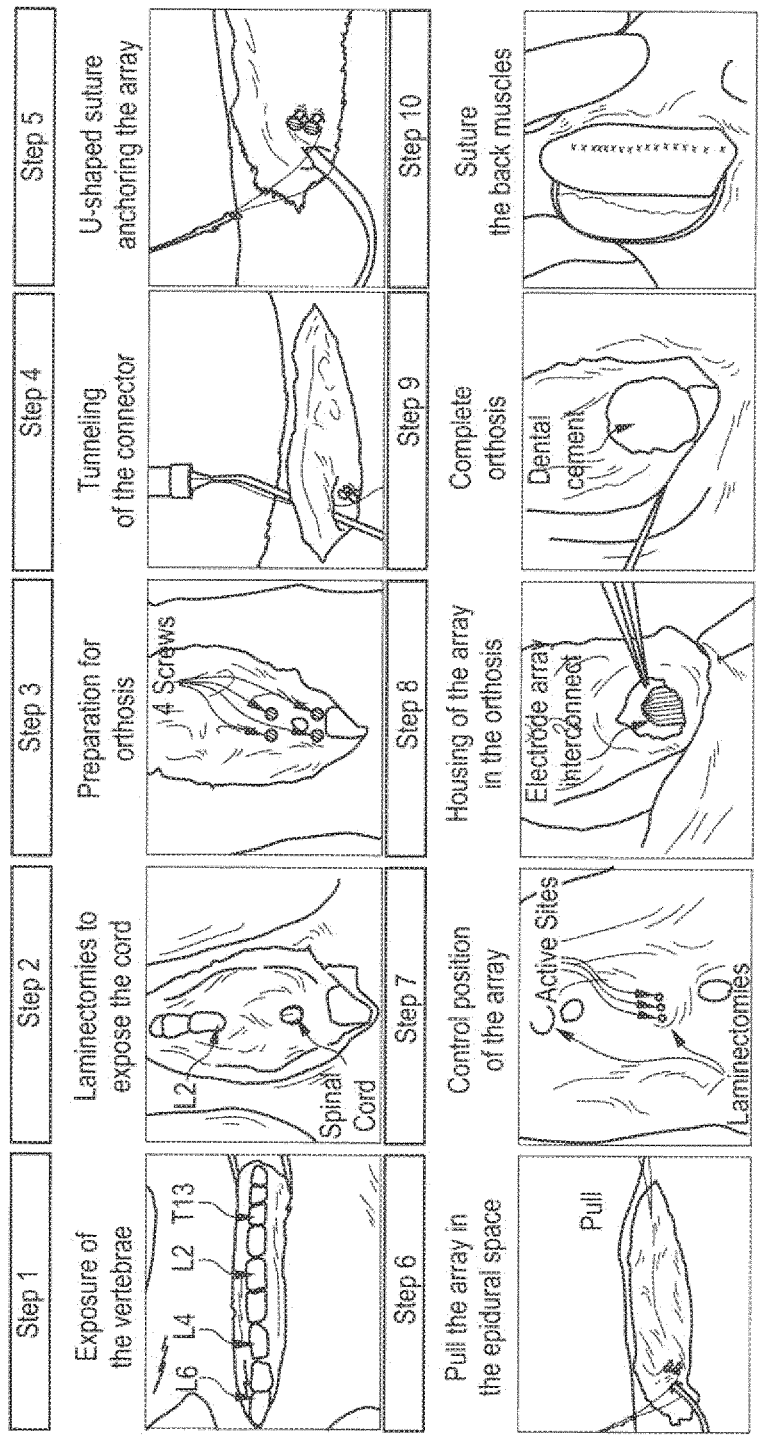
FIG. 5 further steps of implanting an electrode array to the spinal cord.

FIG. 5 shows further steps of implanting an electrode array to the spinal cord.

In step ST100 the exposure of the vertebrae is done.
In step ST110 laminectomies are done to expose the spinal cord.
In step ST120 a preparation for the orthosis is done by using 4 screws.
In step ST140 a tunneling of the connector is prepared and provided.
In step ST 150 a ushape suture is provided for anchoring the electrode array of the neuromodulation lead 22.
In step ST160 the array is pulled into the epidural space.
In step ST170 a control position the array is done.
In step ST180 a housing of the array is provided in the orthosis.
In step ST190 a complete orthosis is performed by using dental cement. This orthosis is used for the rodents to support them during "walking". It is not needed for other mammals like primates (e.g. monkeys or humans).
In step ST200 a suture of the back muscles is provided to close the implantation side.

Figure 6A:
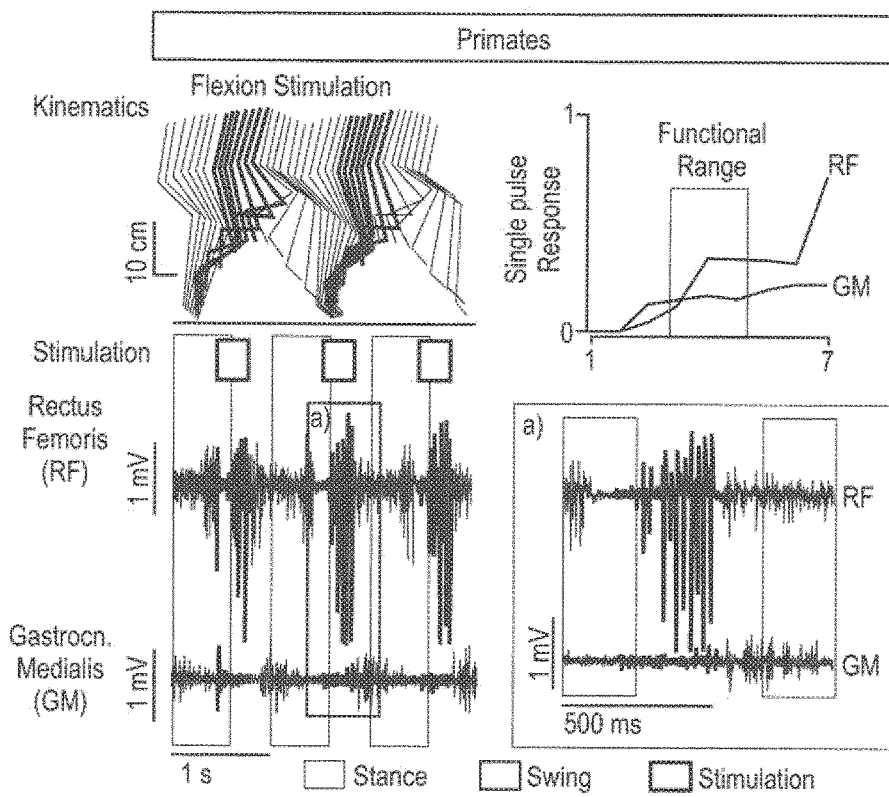
FIG. 6a the kinematics and the stimulation in the functional range on flexion stimulation for primates.
Figure 6B:
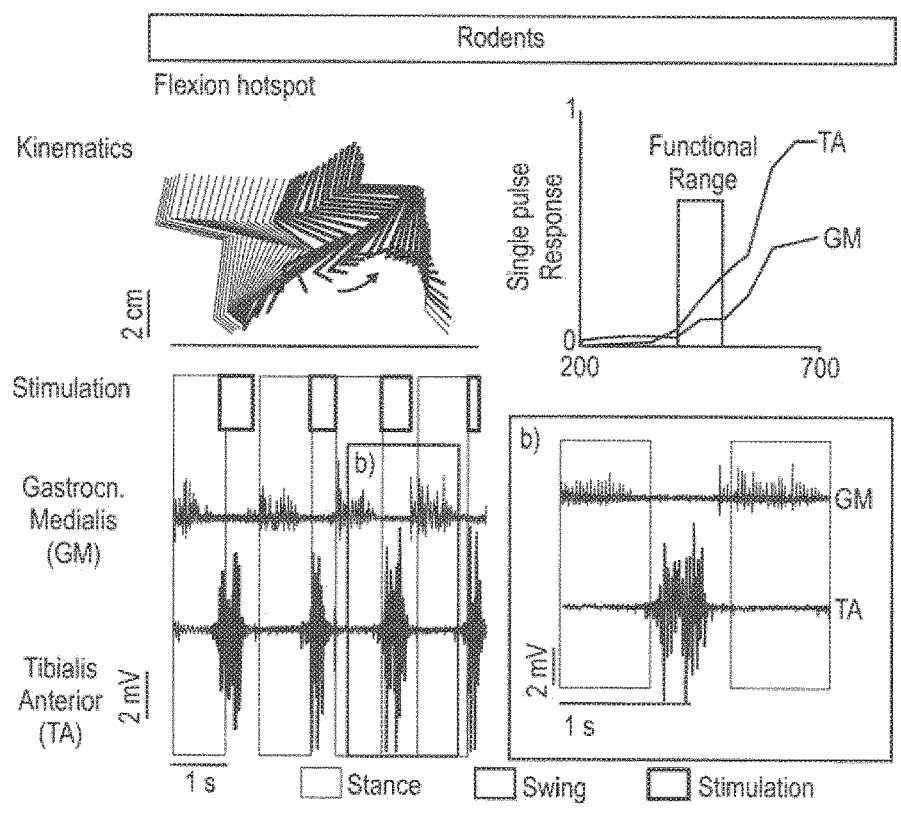
FIG. 6b the kinematics and the stimulation in the functional range on flexion stimulation for rodents.

In FIG. 6a the kinematics and the stimulation in the functional range on flexion stimulation for primates is shown. The corresponding relationship for rodents is shown in FIG. 6b.

Method of Functional Mapping

The method of functional mapping may be performed for example as follows:

Evaluation of the spatial specificity of epidural arrays is achieved by simple electrophysiological testing. A single supra-threshold current pulse of EES, applied through an electrode contact at the lumbosacral level, produces mono- and poly-synaptic electromyographic responses in some leg muscles termed spinal reflexes (FIG. 6a and FIG. 6b).

In particular, the mono-synaptic component of these responses, appearing at the lowest threshold, is related to the direct activation of the Ia afferent fibers. These fibers have excitatory synaptic connections to all the motoneurons of their homonymous muscle. Therefore, given the location of motoneuron pools in the spinal cord (cf. e.g. FIG. 3c and FIG. 3h) and which muscles are activated by single pulses (or low-frequency stimulation, e.g. 0.5-2 Hz) of epidural stimulation, it is possible to infer which roots are stimulated by each of the active sites. This procedure enables to estimate the region of the spinal cord that is preferentially targeted by a specific contact (cf. e.g. FIG. 6a and FIG. 6b).

Indeed, the specificity of epidural arrays for spatiotemporal neuromodulation is not defined by the ability to stimulate single muscles, but rather by the recruitment of specific spinal segments innervating several muscles at the same time. Some antagonist muscles, such as the tibialis anterior and gastrocnemius medialis, may be partially innervated by roots emerging from the same segment. However, spinal circuits and interactions with residual descending control will gate the stimulation effects towards functionally relevant muscles during the execution of a specific movement. The excitability of agonist and antagonist muscles is modulated during gait, resulting in increased functional muscle specificity during movement (cf. e.g. FIG. 6a and FIG. 6b) compared to static measurements. This provides additional robustness in the positioning of the implants. During the implantation procedure, the ability to elicit spinal reflexes in the muscles innervated by the most rostral and the most caudal spinal segments innervating leg muscles (such as the Iliopsoas and Gastrocnemius Medialis respectively) ensures a correct longitudinal placement of the array and a full coverage of the entire lumbosacral spinal cord.

Procedure

Implantation of chronic electromyographic (EMG) electrodes and epidural spinal electrode arrays in rats and primates is done as shown in FIG. 4 and FIG. 5.

For primates or humans the implantation of the neurostimulation lead is done likewise the implantation of electrode arrays for neurostimulation of the spinal cord in connection with pain treatment.

After the implantation, the following exemplary steps for Intra-operative electrophysiology and finalization of the implantation procedure for the epidural array of the neuromodulation lead 22 are performed.

The EMG electrodes are connected and the epidural array to the Real-Time electrophysiology unit.

The system 10 set up to visualize on a monitor and store 50 ms of EMG signals triggered by each stimulation pulse delivered through the epidural array.

Then, the neural stimulator with the neuromodulation pulse generator 24 and the neuromodulation lead 22 is set to current mode (voltage mode can also be used but is not preferred). The stimulation frequency may be chosen at e.g. 0.5 Hz. In general, a current range from 0 to 600 µA in rats and 0 to 5 mA in primates or humans at 200 µs pulse-width may be expected.

After this, one may proceed by stimulating the most rostral sites to verify that the Muscle Evoked Potential of the iliopsoas in response to the epidural stimulation is recruited at lower threshold than the other leg muscles. Stimulation of the most rostral lumbar segments of the spinal cord should induce isolated hip flexion movements associated to each stimulation pulse when the stimulation is applied above motor threshold.

In the next step it is continued by stimulating the most caudal sites to verify that the Muscle Evoked Potential of the Medial Gastrocnemius in both rats and primates (or another most caudally innervated muscle) in response to the epidural stimulation is recruited at lower threshold than other leg muscles. A current amplitude range from e.g. 0 to 300 µA in rats and 0 to 2 mA in primates or humans at 200 µs pulse-width for the stimulation of the caudal spinal cord may be expected. Stimulation of this region should induce isolated ankle dorsi-flexion movements associated to each stimulation pulse when the stimulation is applied above motor threshold.

Then, the longitudinal position of the array may be adjusted by e.g. sliding it under the vertebra and previous steps may be repeated until both conditions are met.

Following to this step/these steps, the medio-lateral positioning of the array is checked by verifying that stimulation of lateral sites at the same spinal level selectively recruits the muscles of the leg ipsilateral to the stimulation site at lower current levels than the muscles of the contralateral leg. The position of the array is adjusted by using the openings provided by the laminectomies at various spinal levels.

Refinement of Electrode Position

Figure 7:
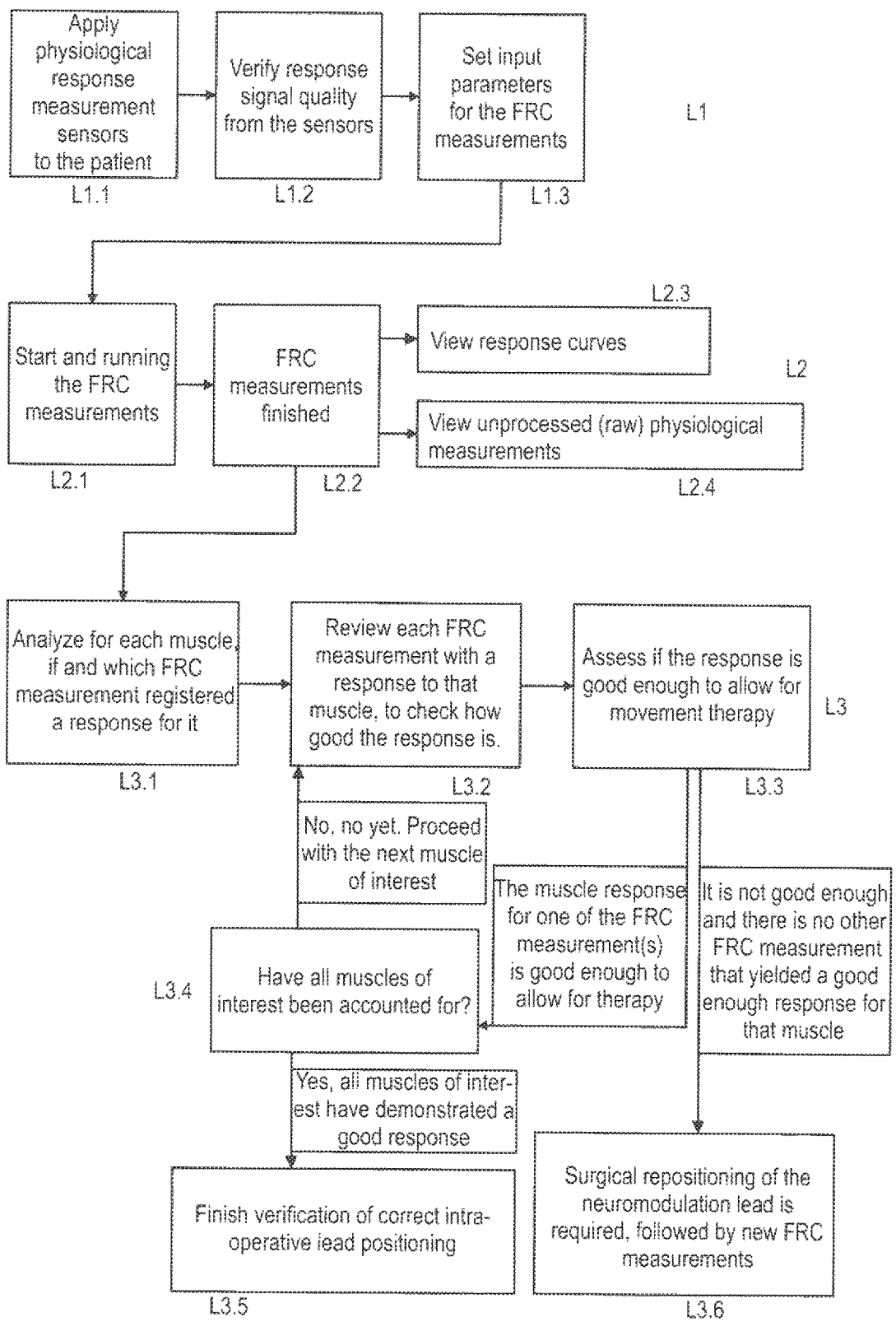
FIG. 7 a workflow for performing the system for planning and/or providing a neuromodulation.

FIG. 7 shows a workflow for performing the system for planning and/or providing a neuromodulation.

In particular, a workflow for performing a postoperative functional recruitment curve measurement for creating a therapy is shown.

Three levels L1, L2 and L3 are shown, wherein level L1 shows the preparation steps, level L2 relates to measuring and reviewing of the functional recruitment curve and level L3 relates to the postoperative use of the functional recruitment curve to create a stimulation for therapy.

Level L1 comprises the steps

"apply physiological response measurement sensors to the patient", i.e. step L1.1, "verify response signal quality from sensors", i.e. step L1.2, "set and put parameters for the FRC measurements", i.e. step L1.3.

In other words, in the steps of level L1 all preparation steps will be performed.

In step L1.1 sensors are applied to the patient to measure the physiological response to the stimulation applied.

In step L1.2 this response is taken and then verified in terms of quality.

After that, in step L1.3, the input parameters for the functional recruitment curve measurements are done.

In particular, in level L1 the electrode array for neurostimulation is implanted and may be also checked regarding its positioning.

Steps L1.1, L1.2 and L1.3 may be iteratively performed again and again, in order to position the electrode array correctly.

In level L2 further steps are done for measuring and reviewing the functional recruitment curves.

The steps of level L2 are:

"start and running the FRC measurements", i.e. step L2.1,

"FRC measurements finished", i.e. step L2.2,

"view of response costs", i.e. step L2.3,

"view of unprocessed (raw) physiological measurements", i.e. L2.4.

For measuring and reviewing the recruitment curves as for example shown in FIG. 2, first the start and running of the FRC measurements must be done in step L2.1. For this, specific measurement routines may be available.

After the functional recruitment curve measurements are finished in step L2.2, the response curves (for example as shown in FIG. 2) may be viewed in step L2.3.

Also, it is possible to perform a review of the unprocessed (raw) physiological measurements.

Especially step L2.4 may give hints to the advanced user and help to find out optimal stimulation parameters.

In the steps of level L3, all steps are performed in the postoperative face. Here, the functional recruitment curves are used to create a stimulation for a therapy and to assist the patient in rehabilitation.

In particular, the functional recruitment curves are used to create an epidural electrical stimulation to help the brain help itself, i.e. to re-organize the signal transfer from the brain and spinal cord.

The steps of level L3 comprise the following steps:

"analyze for each muscle, which FRC measurement registered a response for it", i.e. step L3.1, "review each FRC measurement with a response to that muscle, to check how good the response is", i.e. step L3.2, "assess if the response is good enough to allow for movement therapy", i.e. step L3.3, "have all muscles of interest being accounted for", i.e. step L3.4, "finish verification of correct inter operative lead positioning", i.e. step L3.5 and "surgical repositioning of the neuromodulation lead if required, followed by new FRC measurements", i.e. step L3.6.

In step L3.1, for each muscle, which is needed for a specific movement, an analysis is performed, which functional recruitment curve (FRC) might be suitable and comprises a response for the intended muscle activity.

In step L3.2 each FRC measurement will be reviewed with a response to that muscle, to check, how good the response is. Here, the quality of the response to that muscle is assessed and also checked.

In step L3.3 an assessment is taken, if the response is good enough to allow for movement therapy.

If the response is not good enough and there is no other FRC measurement that yielded a good enough response for that muscle, then it is continued with step L3.6.

Consequently, a surgical repositioning of the neuromodulation lead is required, followed by the new FRC measurements.

If in step L3.3 it is found that the muscle response for (one of) the FRC measurements is good enough to allow for therapy, then it is in step L3.4 checked, whether all muscles of interests have been accounted for, i.e. all necessary muscles have been checked.

If this is the case, then it is continued following step L3.4 with step L3.5, which is finishing the verification of correct inter operative lead positioning.

If not all muscles of interest have been accounted for, then it is proceeded with the next muscle of interest and continued in step L3.2 accordingly.

Spatial Specificity: Post-Surgical selection of optimal electrode configurations Firstly, the epidural spinal stimulation system is set up. In rats, the headplug receiving the wires from the epidural electrode array is connected to to a multichannel stimulator controlled by a computer or real-time processor (e.g. RZ2 Bioamp Processor, Tucker-Davis Technologies). In primates or humans establishing communication with an Implantable Pulse Generator (IPG) (e.g. Activa RC, Medtronic). Communication occurs via a telemetry system consisting of an antenna linked to an interface worn by the animal and placed in a custom-made jacket. This interface should be able to transmit information wirelessly (e.g. by Bluetooth) to an external computer. Such systems with real-time communication capabilities do not readily exist as commercial system but can be used as investigational devices through collaborations with biomedical companies such Medtronic.

Optionally, a video recording or motion capture system may be used to record the movements that will be induced by epidural stimulation (as described in the following point).

The spatial selectivity of the electrode array is characterized following a procedure similar to that described on connection with the verification of the Muscle Evoked Potential of muscles of interest. The stimulation is set by selecting an electrode site and send single bipolar electrical pulses (200-μs pulse width) at a frequency of 0.5 Hz. The electrode site being tested is selected as the cathode (negative polarity).

Then, the stimulation amplitude is manually increased from until a motor evoked potential is observed. A motor potential elicited by the stimulation should occur within about 3-8 ms in the rats and 5-15 ms in the primates after the stimulation pulse. Take note of the minimum intensity eliciting a motor potential as the motor threshold.

The intensity is increased until the motor responses on all muscles saturate in amplitude and take note of the saturation amplitude.

A recording of the EMGs is performed while systematically ramping up the stimulation amplitude from 0.9× the motor threshold found until the saturation amplitude found.

The above steps are repeated for each electrode of the spinal implant, until muscle responses evoked by each of the electrode contacts are recorded.

Optionally, a testing of additional multipolar electrode configurations may be performed. In the case in which leg specificity or muscle specificity is considered insufficient, multipolar configurations can be used to increase it. For example if all the electrodes on the left side of the array induce responses in both limbs, multipolar configurations may be tested with the cathode on the left side and the anode on the midline or on the right side in order to steer the activating field towards the desired limb. Likewise, if there is a lack of rostro-caudal selectivity, for example if the iliopsoas (most rostral muscle) is not specifically recruited by the most rostral electrodes, the cathode may be placed on the most rostral electrode and one or several anodes on the electrodes caudal to it.

When all recordings are completed the local procedures defined for awakening and post-sedation care will be performed.

Then, the recruitment curves and the digital characteristic are calculated and computed offline from the data obtained in the steps described above. Recruitment curves indicate the normalized level of activation of each muscle in response to single electrical pulses of increasing amplitude. The EMG activity is normalized by its maximum across all stimulation amplitudes and all stimulation sites. These recorded motor responses can also be translated into spatial maps of motoneuron pool activation, so-called spinal maps. From the recruitment curves, identify a functional range of stimulation amplitudes in which only the muscles activated at the lowest thresholds are significantly recruited. The spinal maps are computed corresponding to this functional range and use them to define the spatial specificity of each electrode configuration.

By analyzing the computed spinal maps, the electrode configuration is determined that creates the highest activation in the spinal segments responsible for flexion of the leg, especially hip flexion (L1-L2 in rats during bipedal locomotion, L1-L2 in primates) and has unilateral responses over a wide range of amplitudes. This configuration is selected to promote global flexion of the leg. Similarly, the electrode configuration is determined that creates the highest activation in the spinal segments responsible for extension of the leg, especially ankle extension (L4-L6 in rats during bipedal locomotion, L6-L7 in primates) and has unilateral responses over a wide range of amplitudes. This configuration is selected to promote global extension of the leg Time Specificity: Determination of Stimulation Patterns The required timing for each type of stimulation is determined. Prior to the planned experiments, first EMG recordings of a few healthy individuals walking in the same conditions as used for the impaired subjects are performed. From these EMG recordings, the spatiotemporal maps (i.e. digital characteristic maps) of motoneuron activation during healthy locomotion are computed and determined. In rats and primates or humas, the analysis of these spinal maps will reveal that the spinal segments associated with flexion should be activated from the beginning of swing (foot off) to the middle of swing. Similarly, the spinal segments associated with extension should be activated from the beginning of stance ('foot strike') to the middle of stance.

Then, a system is set up, which is able to detect or predict in real-time the gait events necessary for spatiotemporal neuromodulation: "foot off", "foot strike", "mid-stance", "mid-swing". This system can be based on a real-time motion capture system in case there is residual voluntary motor control and if the animal can wear infrared-reflective markers or other types of motion sensors. Otherwise, the instantaneous motor state can be decoded from neural signals using intracortical microelectrode arrays, electro encephalograms (EEG) or implanted EEG (Ecog).

Following to that, the sequence of stimulation bursts is programmed based on the detected gait events. In case all the detected events are sufficiently separated in time, all of them can be used to trigger the onset or the end of a particular set of stimulation bursts. However, if the stimulator can only accept stimulation commands up to a maximum rate and if the time interval between some consecutive events is too short to send two separate commands, an alternative solution is to pre-program the duration of the stimulation bursts. In this solution, the gait events only trigger the onset of stimulation, and the bursts are terminated automatically after a certain time has elapsed.

In a further step, initial amplitudes and frequencies are selected. To start with this procedure, e.g. one can select a frequency of about 60 Hz for all electrode configurations used in the program defined above. For each electrode configuration, one can select an amplitude around 1.5 times the motor threshold obtained during recruitment curves. Closed-loop spatiotemporal neuromodulation may be tested with this set of parameters. The amplitudes may be adjusted based on kinematics and EMG activity. Each electrode configuration should have a significant effect on the targeted muscle group without loss of muscle specificity.

The stimulation timing may be refined empirically. Alternatively, this can be done automatically with simulation tools or the like.

One may anticipate or delay the onset of each stimulation burst and see if the effect on kinematics and EMG activity is improved. Kinematic effects can be quantified by looking at key variables such as step height or stride length, or by computing an exhaustive list of kinematic variables and using dimensionality reduction techniques such as Principal Component Analysis (PCA). Similarly, one may extend or reduce the duration of each stimulation burst and examine the effect on kinematics and EMG activity. The process may be iterated until an optimal set of parameters is found.

Also, stimulation amplitudes and frequencies may be refined. The timing obtained in the previous step may be used. One may then re-adjust the amplitudes and frequencies. Each electrode configuration should have a significant effect on the targeted muscle group without loss of muscle specificity.

Note that the example control and estimation routines included herein can be used with various neuromodulation and/or neurostimulation system configurations. The control methods and routines disclosed herein may be stored as executable instructions in non-transitory memory and may be carried out by the control unit in combination with the various sensors, actuators, and other system hardware in connection with a medical neurostimulation system. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the control unit, where the described actions are carried out by executing the instructions in a system including the various hardware components in combination with a electronic control unit.

Explicitly disclosed in connection with the above disclosure is the following aspect:

1. A method for planning and/or providing neuromodulation, including neurostimulation, comprising linking and/or translating stimulation related basic data into and/or with response data and/or artificial response data to generate transfer data, the transfer data comprising link data and/or translation data and/or artificial response data, generating a digital characteristic map based on stimulation related basic data and stimulation related response data and the transfer data, the digital characteristic map describing an interrelation between the stimulation related basic data and the stimulation related response data and the transfer data; and generating neuromodulation signals via an actuator based on the digital characteristic map.

2. The method according to aspect 1, wherein the method further comprises applying machine learning to generate the characteristic map.

REFERENCES 10 neuromodulation and/or neurostimulation system
12 physiological response measurement sensor
14 physiological response measurement receiver and processor
16 computer
18 software
20 visualization module
22 neuromodulation lead
24 neuromodulation pulse generator
26 first data input module
28 stimulation related basic data storage module
30 second data input module
32 stimulation related response data storage module
34 transfer module
36 digital characteristic map
38 mapping module
40 virtual mapping module
42 correlation and/or simulation module, analysis module
44 neuromodulation settings generation module
46 transfer interface
M1 first muscle M2 second muscle
P patient
P1 onset point
P2 saturation point
P3 specificity point
P1' onset point
P2' saturation point
S storage

The invention claimed is:

1. A system for planning and/or providing spinal cord stimulation comprising:
 a neurostimulator comprising at least one electrode;
 a functional mapping module configured to:
  generate a digital characteristic functional map based on stimulation related basic data, stimulation related response data, and transfer data, wherein, the digital characteristic functional map describes an interrelation between the stimulation related basic data, the stimulation related response data, and the transfer data; and
 an analysis module configured to:
  analyze the digital characteristic functional map in connection with neurostimulation of a spinal cord by the neurostimulator;
  analyze the neurostimulation of the spinal cord and a spinal cord response based on the digital characteristic functional map; and
  analyze a placement of the at least one electrode based on the analysis of the neurostimulation and the spinal cord response.

2. The system according to claim 1, further comprising a stimulation related basic data storage module for storing stimulation related basic data defining parameters of the neurostimulator for treating a patient, the stimulation related basic data storage module comprising at least one set of stimulation related basic data and/or working parameters of the neurostimulator.

3. The system according to claim 1, further comprising:
 a stimulation related response data storage module for storing the stimulation related response data, the stimulation related response data storage module comprising at least one set of stimulation related response data including activation of the spinal cord in response to stimulation provided to the spinal cord.

4. The system according to claim 1, further comprising:
 a data input module configured to receive the stimulation related basic data;
 a transfer module configured to:
  link and/or translate the stimulation related basic data received by the data input module into the stimulation related response data or artificial response data created by the transfer module, wherein data generated by the transfer module are transfer data, the transfer data comprising link data and/or translation data and/or the artificial response data and/or reference data, and
 a transfer response data storage module for storing the transfer data.

5. The system according to claim 1, further comprising a visualization module.

6. The system according to claim 5, wherein the visualization module is configured to display at least partially stimulation related basic data and at least partially stimulation related response data.

7. The system according to claim 5, wherein the visualization module is configured to schematically visualize the stimulation related response data with representations of muscles and/or muscle groups receiving neurostimulation.

8. The system according to claim 1, further comprising:
 a stimulation related response data input module, wherein the system is configured to provide an inverse control by inputting stimulation related response data via the stimulation related response data input module, and
 a selection module configured to select suitable stimulation related basic data based on the digital characteristic functional map.

9. The system according to claim 1, further comprising:
 a neuromodulation settings generation module configured to translate the digital characteristic functional map into neuromodulation parameter settings for a neuromodulation treatment of a subject.

10. The system according to claim 9, further comprising a transfer interface configured to transfer neuromodulation parameter settings to the neurostimulator.

11. The system according to claim 1, wherein the analysis module is configured to generate a placement proposal based on the functional map and the analysis of the placement.

12. The system according to claim 11, wherein the placement proposal is displayed by a visualization module.

13. A method for planning and/or providing neuromodulation of a spinal cord, comprising:
 linking and/or translating stimulation related basic data into and/or with stimulation related response data and/or artificial response data to generate transfer data, the transfer data comprising link data and/or translation data and/or the artificial response data;
 generating a digital characteristic map based on the stimulation related basic data, the stimulation related response data, and the transfer data, the digital characteristic map describing an interrelation between the stimulation related basic data, the stimulation related response data and the transfer data;
 generating a placement proposal for placement of at least one electrode providing neurostimulation of the spinal cord based on the digital characteristic map; and
 outputting the placement proposal via one or more of a display, a loudspeaker, a beamer, and a projector.

* * * * *